United States Patent
Kumagai et al.

[11] Patent Number: 5,250,641
[45] Date of Patent: Oct. 5, 1993

[54] CURING OF DENTAL RESIN

[75] Inventors: Tomohiro Kumagai, Kasugai; Akira Hasegawa, Inuyama, both of Japan

[73] Assignee: GC Dental Products Corp., Kasugai, Japan

[21] Appl. No.: 863,416

[22] Filed: Apr. 3, 1992

[30] Foreign Application Priority Data

Nov. 13, 1991 [JP] Japan .................. 2-324111

[51] Int. Cl.⁵ .................. C08F 4/44; C08F 120/18
[52] U.S. Cl. .................. 526/141; 526/192; 526/204; 526/329.7
[58] Field of Search .................. 526/141

[56] References Cited

U.S. PATENT DOCUMENTS 4,873,269 10/1989 Nakazato .................. 523/115
4,880,887 11/1989 Hasegawa .................. 526/141

FOREIGN PATENT DOCUMENTS 2193967 2/1988 United Kingdom.
2202543 9/1988 United Kingdom.

OTHER PUBLICATIONS

R. Epton, P. Goddard, G. Marr, J. V. McLaren and G. J. Morgan, Polymer 20, 1444-1446, 1979.

Primary Examiner—Joseph L. Schofer
Assistant Examiner—Wu C. Cheng
Attorney, Agent, or Firm—Oblon, Spivak, McClelland, Maier & Neustadt

[57] ABSTRACT

A method of curing dental resin according to this invention is characterized by adding a morpholine derivative to a conventional curing process, more particularly, the dental resin is cured by polymerizing (1) a polymerizable compound having at least one ethylenically unsaturated double bond in the presence of (2) a morpholine derivative, (3) 1-cyclohexyl-5-ethylpyrimidinetrione, (4) an organometal compound and (5) an organohalogen compound, in which the self-polymerizing dental resin is polymerized or cured more rapidly than is possible with the conventional process and without detriment to its transparency, color tone stability and physical properties.

10 Claims, 1 Drawing Sheet

CURING OF DENTAL RESIN

BACKGROUND OF THE INVENTION

The present invention relates generally to curing self-polymerizing resin for dental purposes and more particularly to improving on the curing rate of a conventional resin system using a pyrimidinetrione derivative as a polymerization initiator and various organometal and organohalogen compounds as promoters, without detriment to its own characteristic features such as transparency, color tone stability and physical properties.

In recent years, self-polymerizing dental resin systems have generally been used, which rely upon a pyrimidinetrione derivative as a polymerization initiator and various organometal and organohalogen compounds as promoters. These resin systems have been known to be better than those relying on organic peroxides as polymerization initiators and aromatic tertiary amines as promoters in terms of transparency, color tone stability and physical properties, but are still subject to a problem that their polymerizing/curing rate is unacceptably slow.

An object of this invention is therefore to provide a solution to a slow polymerizing/curing rate problem associated with self-polymerizing resins without detriment to the transparency and color tone stability characteristic of the cured products, using a pyrimidinetrione derivative as a polymerization initiator and organometal and organohalogen compounds as promoters.

SUMMARY OF THE INVENTION

We have now found after study that all the defects of conventional dental resins can be eliminated by curing a polymerizable compound having at least one ethylenically unsaturated double bond in the presence of 1-cyclohexyl-5-ethylpyrimidinetrione, an organometal compound and an organohalogen compound as well as a morpholine derivative. That is, we could provide a solution to such a slow polymerizing/curing rate problem as found in the conventional systems comprising 1-cyclohexyl-5-ethylpyrimidinetrione, an organometal compound and an organohalogen compound without detriment to color tone stability and physical properties.

DETAILED DESCRIPTION OF THE INVENTION

The morpholine derivatives used preferably in this invention, for instance, include morpholine, acryloylmorpholine, N-acetoacetylmorpholine, N-$\beta$-hydroxyethylmorpholine, N-(2-hydroxypropyl)morpholine, N-(3-aminopropyl) morpholine and N-(2-aminoethyl)morpholine. It is noted, however, that for the polymerization of the polymerizable compound having at least one ethylenically unsaturated double bond, preference is given in particular to acryloylmorpholine and N-acetoacetylmorpholine.

Preferably, the quantity of the morpholine derivative used lies in the range of 0.1 to 15 parts by weight per 100 parts by weight of the polymerizable compound having at least one ethylenically unsaturated double bond. Falling short of 0.1 part by weight is unsuitable because no accelerated curing takes place. Again, exceeding 15 parts by weight is unsuitable for dental self-polymerizing resin, because the morpholine derivative gives out its own odor and the cured product may often be colored, thus found not suitable for the purpose.

Among a number of pyrimidinetrione derivatives, the most effective is 1-cyclohexyl-5-ethyl-pyrimidinetrione.

In addition to 1-cyclohexyl-5-ethylpyrimidinetrione, N-benzyl-5-phenylpyrimidinetrione, 5-butyl-pyrimidinetrione, 5-phenyl-pyrimidinetrione, 5,5-diethylpyrimidinetrione, 1,3,5-trimethyl-pyrimidinetrione, 2,4,6-(1H,3H,5H)-pyrimidinetrione and 1,3-dimethylpyrimidinetrione are generally known as the pyrimidinetrione derivatives, Because of such drawbacks as mentioned just below, however, they cannot be used for intra-oral applications obtained by the polymerization of the polymerizable compounds having at least one ethylenically unsaturated double bond.

In other words, the use of N-benzyl-5-phenylpyrimidinetrione, 5-butylpyrimidinetrione or 1,3,5-trimethylpyrmidinetrione causes the cured product to be clouded in white, the resin system to be cured being too slow to lend itself fit for rapid-curing purposes. The use of 5-phenylpyrimidinetrione or 5-ethylpyrimidinetrione takes a period as long as about 1 day for the resin system to be cured at room temperature as does the use of 1,3-dimethylpyrimidinetrione. In the latter case, the cured product shows a reddish brown color, thus failing to be used. Nor is any curing catalyst action obtained by the use of 5,5-diethyl-pyrimidinetrione or 2,4,6-(1H,3H,5H)-pyrimidinetrione.

The use of 1-cyclohexyl-5-ethylpyrimidinetrione, however, enables the polymerizable compound having at least one ethylenically unsaturated double bond to be cured within a curing time that merits a rapid-curing, say, 6.5 minutes, and provides a transparent or glassy cured product. This means that the cured product could be colored in any desired color since it is as transparent as glass. Furthermore, the resulting cured product can be applied within the intra-oral condition without suffering discoloration or coloration and with much more improved physical properties.

Preferably, the quantity of 1-cyclohexyl-5-ethylpyrimidinetrione used lie in the range of 0.1 to 10 parts by weight per 100 parts by weight of the polymerizable compound having at least one ethylenically unsaturated double bond. Both falling short of 0.1 part by weight and exceeding 10 parts by weight result in a slow curing rate and so are unsuitable for the self-polymerizing dental resins required to be rapidly cured.

When the polymerizable compound having at least one ethylenically unsaturated double bond is polymerized using 1-cyclohexyl-5-ethylpyrimidinetrione, the temperature at which the heat of polymerization is generated is about 8° C. lower when compared with the polymerization taking place through a conventional combination of benzoyl peroxide with an aromatic tertiary amine—as measured with a powder/liquid mixture at a ratio of 2 g/1 g respectively, thus making it possible to reduce thermal stimulations to a patient's mouth in case of directly rebase.

The term "a polymerizable compound having at least one ethylenically unsaturated double bond" used herein is understood to refer to a compound of chemical morphology such as that represented by a monomer and a prepolymer (i.e., a dimer, trimer or other oligomer) as well as a mixture or a copolymer thereof.

Specific, but not exclusive, reference is made to monomers having one ethylenically unsaturated double bond, e.g., methyl methacrylate, ethyl methacrylate, iso-propyl methacrylate, hydroxyethyl methacrylate, tetrahydrofulfuryl methacrylate, glycidyl methacrylate and their acrylate; and monomers having two ethylenically unsaturated double bond, e.g., aromatic ones such as 2,2-bis(methacryloxyphenyl)propane, 2,2-bis[4-(2-hydroxy-3-methacryloxyphenyl)propane, 2,2-bis(4-methacryloxyethoxy-phenyl)propane, 2,2-bis(methacryloxydiethoxyphenyl)propane or 2,2-bis(4-methacryloxypropoxy-phenyl)propane or their acrylates and aliphatic ones such as ethylene glycol dimethacrylate, diethylene glycol dimethacrylate, triethylene glycol dimethacrylate, butylene glycol dimethacrylate, neopentyl glycol dimethacrylate, 1,3-butanediol dimethacrylate, 1,4-butanediol dimethacrylate, 1,6-hexanediol dimethacrylate or their acrylates.

The monomers having three ethylenically unsaturated double bonds, for instance, may include trimethylolpropane trimethacrylate, trimethylolethane trimethacrylate, pentaerythritol trimethacrylate, trimethylolmethane trimethacrylate and their acrylates thereof. The monomers having four ethylenically unsaturated double bonds, for example, may include pentaerythritol tetramethacrylate, pentaerythritol tetra-acrylate, 1,6-bis[1,3-bis(methacryloyloxy)-2-(propoxycarbonylamino)] hexane and 1,6-bis[1,3-bis(acryloyloxy)-2-(propoxycarbonylamino)]hexane.

The monomers having six ethylenically unsaturated double bonds, for instance, may include 1,3,5-tris[1,3-bis(methacryloyloxy)-2-(propoxycarbonylamino)hexane]-1,3,5-(1H,3H,5H) triazine-2,4,6-trione and 1,3,5-tris[1,3-bis(acryloyloxy)-2-(propoxycarbonylamino)-hexane]-1,3,5-(1H,3H,5H)triazine-2,4,6-trione.

The organometal compounds used, for instance, may include acetylacetone copper, copper 4-cyclohexyl butyrate, copper acetate, copper oleate, copper gluconate, acetylacetone manganese, manganese naphthenate, manganese octylate, acetylacetone cobalt (III), cobalt naphthenate, acetylacetone lithium, lithium acetate, acetylacetone zinc, zinc naphthenate, acetylacetone nickel, nickel acetate, acetylacetone aluminium, acetylacetone calcium, acetylacetone chromium (III), acetylacetone iron (III), sodium naphthenate and rare earth octoate, which may be used alone or in admixture. Among others, the preference is given in particular to acetylaceton copper and copper 4-cyclohexyl butyrate.

Preferably, the quantity of the organometal compounds used lies in the range of 0.001 to 0.2 parts by weight per 100 parts by weight of the polymerizable compound having at least one ethylenically unsaturated double bond. 0.001 or less part by weight, it is too poor in reactivity to obtain a rapid- and self-polymerizing dental resin, whereas 0.2 or more parts by weight it shows colors peculiar to the organometal compound, e.g., blue in the case of acetylacetone copper and reddish brown in the case of acetylacetone iron (III).

The organohalogen compounds used for this invention, for instance, may include dilauryldimethyl ammonium chloride, trioctylmethyl ammonium chloride, benzyldimethylcetyl ammonium chloride, benzyldimethylstearyl ammonium chloride, lauryldimethylbenzyl ammonium chloride, benzyltrimethyl ammonium chloride, diisobutylamine hydrochloride, tetra-n-butyl ammonium chloride, triethylamine hydrochloride, trimethylamine hydrochloride, dimethylamine hydrochloride, diethylamine hydrochloride, methylamine hydrochloride, ethylamine hydrochloride, iso-butylamine hydrochloride, β-phenylethylamine hydrochloride, acetylcholin chloride, 2-chlorotriethylamine hydrochloride, (2-chloroethyl)trimethyl ammonium chloride, tetradecyldimethylbenzyl ammonium chloride, tetraethyl ammonium chloride, tetramethyl ammonium chloride, tetrabutyl ammonium bromide, benzyltrimethyl ammonium bromide, benzyltriethyl ammonium bromide, tetrabutyl ammonium fluoride, tetrabutyl ammonium iodide, tetramethyl ammonium chloride and benzyltriethyl ammonium chloride, which may be used alone or in admixture.

Among these organohalogen compounds, six, say, dilauryldimethyl ammonium chloride, lauryldimethylbenzyl ammonium chloride, tetra-n-butyl ammonium chloride, trioctylmethyl ammonium chloride, benzyldimethylcetyl ammonium chloride and benzyldimethylstearyl ammonium chloride are preferred, because they are soluble at normal temperature in an amount of up to about 5 parts by weight per 100 parts by weight of the polymerizable compound having at least one ethylenically unsaturated double bond. Note that other organohalogen compounds must be filtered for use, because their solubilities are very low at normal temperature.

Preferably, the quantity of the organohalogen compounds used lie in the range of 0.1 to 5 parts by weight per 100 parts by weight of the polymerizable compound having at least one ethylenically unsaturated double bond. Below 0.1 part by weight it is too poor in reactivity to obtain a rapid- and self-polymerizing dental resin. Above 5 parts by weight, by contrast, it allows the resin system to be cured within a certain span of time but gives rise to much heat during the polymerization of the polymerizable compound, failing to meet the quality needed for, e.g., a rebase material applied directly in the oral. In addition, it shows its own color, e.g., pale yellow in the case of dilauryldimethyl ammonium chloride. Thus, no colorless, transparent cured product can be obtained at all.

In some cases, fillers may be used for the purpose of bettering the physical properties of the polymerized/cured product. To this end, any desired fillers, whether of an inorganic, organic or hybrid type, may be used. By way of example alone, mentioned are so-called organic hybrid fillers obtained by compacting powdery quartz, powdery alumina, powdery glass, kaolin, talc, calcium carbonate, barium aluminosilicate glass, titanium oxide, borosilicate glass or colloidal silica with a polymer, followed by pulverization; whisker forms of alumina, beryllium oxide, boron carbide, silicon carbide, silicon nitride and various metals (chromium, copper, iron, nickel) and so on. The powdery polymers used, for instance, may be polymethyl acrylate, polymethyl methacrylate, polyethyl methacrylate, a copolymer of methyl methacrylate with ethyl methacrylate, a crosslinked type of polymethyl methacrylate, a copolymer of ethylene with vinyl acetate, a copolymer of styrene with butadiene, a copolymer of acrylonitrile with styrene and acrylonitrile-styrene-butadiene copolymer, which may, in some cases, be used in the form of an admixture with the above inorganic powders or organic hybrid fillers.

Prior to mixing the inorganic filler with binder resin, it is preferred that they be treated with a coupling agent capable of reacting with the filler and the binder resin. The coupling agents used to this end, for instance, may include those based on organo-functional silanes, titanates and aluminates. Alternatively, the inorganic filler may be grafted on its surface for coupling to the binder resin.

As the organofunctional silane coupling agents, for instance, use may be made of γ-methacryloxypropyltrimethoxysilane, vinyltrichlorosilane, vinyl-tris(β-methoxyethoxy) silane, γ-methacryloxypropylmethyl dimethoxy silane, γ-glycidoxypropyltrimethoxysilane, γ-chloropropyltrimethoxysilane, β-(3,4-epoxycyclohexyl)ethyltrimethoxysilane, trimethylchlorosilane, dimethyldichlorosilane, hexamethyldisilane, γ-aminopropyltriethoxysilane, N-β-(aminoethoxy)-γ-aminopropyltrimethoxysilane and γ-ureidpropyltrimethoxysilane.

How to carry out the surface treatment with these coupling agents is not critical. Although not generally defined because of the varying properties demanded, the quantities of such coupling agents used lie suitably in the range of 0.1 to 20 parts by weight, preferably 1~10 parts by weight per 100 parts by weight of the inorganic material.

In the ensuing description, examples according to this invention and comparative examples will be given; however, bear in mind that this invention is by no means limited to them.

EXAMPLES 1-12

In these examples, methyl methacrylate that is a typical monomer having one ethylenically unsaturated double bond was cured with the use of combinations of the morpholine derivatives, 1-cyclohexyl-5-ethylpyrimidinetrione, organo-metal compounds and organohalogen compounds used preferably in this invention.

COMPARATIVE EXAMPLE 1

For the purpose of comparison, the monomer was cured by the conventional combination of benzoyl peroxide with dimetyl p-toluidine.

COMPARATIVE EXAMPLE 2-5

For the purpose of comparison, the morpholine derivative was used in amounts departing from the preferable scope defined in this invention.

It is noted that how to test and what was tested are set out and illustrated in Table 1 and FIG. 1 and the results of experimentation are set out in Table 5.

TABLE I

Figure 1:
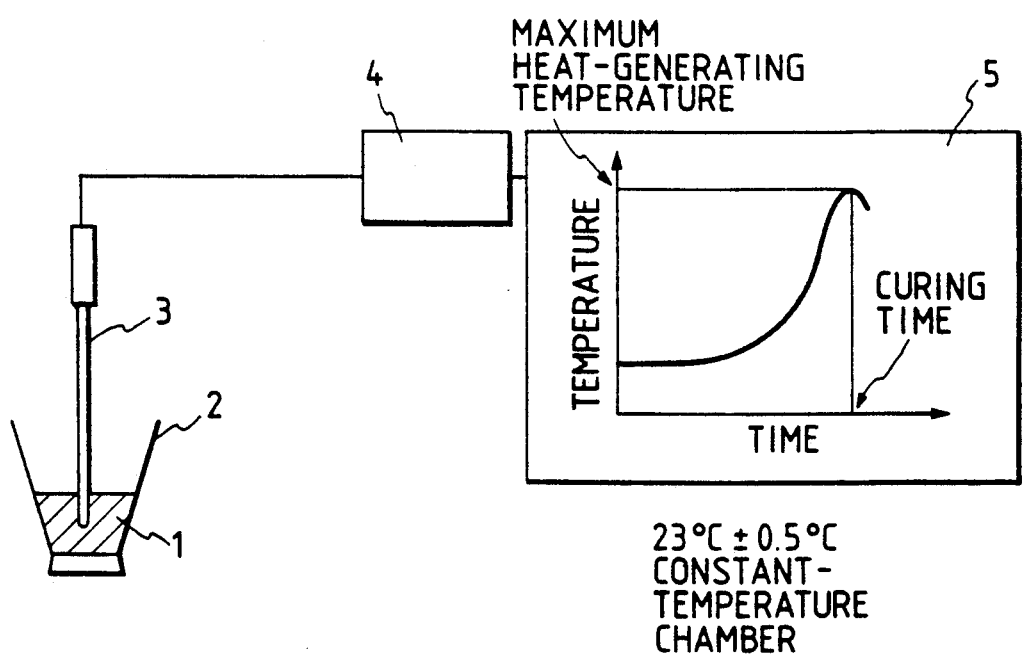
FIG. 1 is a schematic sketch illustrating how to determine curing time and the maximum heat-generating temperature. Reference numeral 1 stands for a powder/liquid mixture, 2 a silicone rubber cup, 3 a thermistor thermometer, 4 an amplifier and 5 a recorder showing the temperature-to-time relation, on which the curing time and the maximum heat-generating temperature are displayed.

| | What was Tested and How to Test | | |
|---|---|---|---|
| What was Tested | Testing Environment | Amounts of Powder/Liquid | How to Measure |
| Transparency | Room Environment | Powder/Liquid = 2 g/1 g | Visual Observation |
| Color of Cured Product | Room Environment | Powder/Liquid = 2 g/1 g | Visual observation |
| Curing Time | 23° C. ± 0.5° C. | Powder/Liquid = 2 g/1 g | Heat Generation by Thermistor Thermometer |
| Maximum Heat Generation Temperature | 23° C. ± 0.5° C. | Powder/Liquid = 2 g/1 g | |

EXAMPLES 1-6

| | PARTS BY WEIGHT |
|---|---|
| POWDER PREPARATION | |
| MMA-EMA copolymer | 29 |
| MMA polymer | 70 |
| 1-cyclohexyl-5-ethylpyrimidinetrione | 1 |
| Acetylacetone copper | 0.001 |
| LIQUID PREPARATION | |
| Methyl methacrylate | 92.5 |
| 1,3,5-tris[1,3-bis(methacryloyloxy)-2-(propoxycarbonylamino)hexane]-1,3,5-(1H,3H,5H) triazine-2,4,6-trione | 2 |
| Dilauryldimethyl ammonium chloride | 0.25 |
| Butyl hydroxytoluene | 75 ppm |
| UV absorber | 0.25 |

The morpholine derivatives used are set out in Table 2.

TABLE 2

| | Morpholine Derivatives | |
|---|---|---|
| Example 1 | Acryloylmorpholine | 5 parts by weight |
| Example 2 | Acryloylmorpholine | 0.2 parts by weight |
| Example 3 | Acryloylmorpholine | 14 parts by weight |
| Example 4 | N-acetoacetylmorpholine | 5 parts by weight |
| Example 5 | N-acetoacetylmorpholine | 0.2 parts by weight |
| Example 6 | N-acetoaoetylmorpholine | 14 parts by weight |

EXAMPLES 7-12

| | PARTS BY WEIGHT |
|---|---|
| POWDER PREPARATION | |
| MMA-EMA copolymer | 29 |
| MMA polymer | 70 |
| 1-cyclohexyl-5-ethylpyrimidinetrione | 1 |
| Copper 4-cyclohexyl butyrate | 0.001 |
| LIQUID PREPARATION | |
| Methyl methacrylate | 92.5 |
| 1,3,5-tris[1,3-bis(methacryloyloxy)-2-(propoxycarbonylamino)hexane]-1,3,5-(1H,3H,5H) triazine-2,4,6-trione | 2 |
| Dilauryldimethyl ammonium chloride | 0.25 |
| Butyl hydroxytoluene | 75 ppm |
| UV absorber | 0.25 |

The morpholine derivatives used are set out in Table 3.

TABLE 3

| | Morpholine Derivatives | |
|---|---|---|
| Example 7 | Acryloylmorpholine | 5 parts by weight |
| Example 8 | Acryloylmorpholine | 0.2 parts by weight |
| Example 9 | Acryloylmorpholine | 14 parts by weight |

TABLE 3-continued

| | Morpholine Derivatives | |
|---|---|---|
| Example 10 | N-acetoacetylmorpholine | 5 parts by weight |
| Example 11 | N-acetoacetylmorpholine | 0.2 parts by weight |
| Example 12 | N-acetoacetylmorpholine | 14 parts by weight |

COMPARATIVE EXAMPLE 1

| | PARTS BY WEIGHT |
|---|---|
| POWDER PREPARATION | |
| MMA-EMA copolymer | 100 |
| B.P.O. | 1 |
| LIQUID PREPARATION | |
| Methyl methacrylate | 96.75 |
| 1,3,5-tris[1,3-bis(methacryloyloxy)-2-(propoxycarbonylamino)hexane]-1,3,5-(1H,3H,5H)triazine-2,4,6-trione | 2 |
| Dimethyl p-toluidine | 1 |
| Butyl hydroxytoluene | 75 ppm |
| UV absorber | 0.25 |

COMPARATIVE EXAMPLE 2

| | PARTS BY WEIGHT |
|---|---|
| POWDER PREPARATION | |
| MMA-EMA copolymer | 29 |
| MMA polymer | 70 |
| 1-cyclohexyl-5-ethylpyrimidinetrione | 1 |
| Acetylacetone copper | 0.001 |
| LIQUID PREPARATION | |
| Methyl methacrylate | 92.5 |
| 1,3,5 tris[1,3-bis(methacryloyloxy)-2-(propoxycarbonylamino)hexane]-1,3,5-(1H,3H,5H)triazine-2,4,6-trione | 2 |
| Dilauryldimethyl ammonium chloride | 0.25 |
| Butyl hydroxytoluene | 75 ppm |
| UV absorber | 0.25 |

COMPARATIVE EXAMPLES 3–6

| | PARTS BY WEIGHT |
|---|---|
| POWDER PREPARATION | |
| MMA-EMA copolymer | 29 |
| MMA polymer | 70 |
| 1-cyclohexyl-5-ethylpyrimidinetrione | 1 |
| Acetylacetone copper | 0.001 |
| LIQUID PREPARATION | |
| Methyl methacrylate | 67.5–97.49 |
| 1,3,5-tris[1,3-bis(methacryloyloxy)-2-(propoxycarbonylamino)hexane]-1,3,5-(1H,3H,5H)triazine-2,4,6-trione | 2 |
| Dilauryldimethyl ammonium chloride | 0.25 |
| Butyl hydroxytoluene | 75 ppm |
| UV absorber | 0.25 |

The morpholine derivatives used are set out in Table 4.

TABLE 4

| | Morpholine Derivatives | |
|---|---|---|
| Comparative Example 3 | Acryloylmorpholine | 0.01 parts by weight |
| Comparative Example 4 | Acryloylmorpholine | 30 parts by weight |
| Comparative Example 5 | N-acetoacetylmorpholine | 0.01 parts by weight |
| Comparative Example 6 | N-acetoacetylmorpholine | 30 parts by weight |

TABLE 5

| | Results of the Test | | | |
|---|---|---|---|---|
| | Transparency | Color of Cured Product | Curing Time | Maximum Heat Generation Temperature |
| Example 1 | Good | Colorless | 3'30" | 70° C. |
| Example 2 | Good | Colorless | 3'45" | 70° C. |
| Example 3 | Good | Colorless | 3'00" | 70° C. |
| Example 4 | Good | Colorless | 3'30" | 68° C. |
| Example 5 | Good | colorless | 3'45" | 70° C. |
| Example 6 | Good | Colorless | 3'00" | 70° C. |
| Example 7 | Good | Colorless | 3'30" | 70° C. |
| Example 8 | Good | Colorless | 3'45" | 70° C. |
| Example 9 | Good | Colorless | 3'00" | 70° C. |
| Example 10 | Good | Colorless | 3'30" | 70° C. |
| Example 11 | Good | Colorless | 3'45" | 70° C. |
| Example 12 | Good | Colorless | 3'00" | 70° C. |
| Comparative Example 1 | Bad | Yellow | 5'00" | 77° C. |
| Comparative Example 2 | Good | Colorless | 4'00" | 70° C. |
| Comparative Example 3 | Good | Colorless | 4'00" | 70° C. |
| Comparative Example 4 | Bad | Pale Yellow | 8'30" | 70° C. |
| Comparative Example 5 | Good | Colorless | 4'00" | 70° C. |
| Comparative Example 6 | Bad | Pale Red | 9'00" | 70° C. |

According to Example 1 wherein acetylacetone copper was used as an organometal compound with the addition of 5 parts by weight of acryloylmorpholine, a colorless, transparent cured product could be obtained with a curing time as short as 3.5 minutes.

According to Example 2 wherein acetylacetone copper was used as an organometal compound with the addition of acryloylmorpholine in an amount of 0.2 parts by weight that is close to the lower limit of the quantitative range preferred in this invention, some effect on increasing the curing rate could be found.

According to Example 3 wherein acetylacetone copper was used as an organometal compound with the addition of acryloylmorpholine in an amount of 14 parts by weight that is close to the upper limit of the quantitative range preferable in this invention, the resulting cured product excelled in both transparency and color.

According to Example 4 wherein acetylacetone copper was used with the addition of 5 parts by weight of N-acetoacetylmorpholine, a colorless, transparent cured product could be obtained with a curing time as short as 3.5 minutes.

According to Example 5 wherein acetylacetone copper was used as an organometal compound with the addition of N-acetacetylmorpholine in an amount of 0.2 parts by weight that is close to the lower limit of the quantitative range preferable in this invention, an accelerated curing could be achieved.

According to Example 6 wherein acetylacetone copper was used as an organometal compound with the addition of N-acetoacetylmorpholine in an amount of 14 parts by weight that is close to the upper limit of the quantitative range preferable in this invention, the resulting cured product excelled in both transparency and color.

According to Example 7 wherein copper 4-cyclohexyl butyrate was used as an organometal compound with the addition of 5 parts by weight of acryloylmorpholine, a colorless, transparent cured product could be obtained with a curing time reduced to 3.5 minutes.

According to Example 8 wherein copper 4-cyclohexyl butyrate was used as an organometal compound with the addition of acryloylmorpholine in an amount of 0.2 parts by weight that is close to the lower limit of the quantitative range preferable in this invention, an accelerated curing could take place.

According to Example 9 wherein copper 4-cyclohexyl butyrate was used as an organometal compound with the addition of acryloylmorpholine in an amount of 14 parts by weight that is close to the upper limit of the quantitative range preferable in this invention, the resulting cured product excelled in both transparency and color.

According to Example 10 wherein copper 4-cyclohexyl butyrate was used as an organometal compound with the addition of 5 parts by weight of N-acetoacetylmorpholine, a colorless, transparent cured product could be obtained with a curing time reduced to 3.5 minutes.

According to Example 11 wherein copper 4-cyclohexyl butyrate was used as an organometal compound with the addition of N-acetoacetylmorpholine in an amount of 0.2 parts by weight that is close to the lower limit of the quantitative range preferable in this invention, some effect on increasing the curing rate could be found.

According to Example 12 wherein copper 4-cyclohexyl butyrate was used as an organometal compound with the addition of 14 parts by weight that is close to the upper limit of the quantitative range preferable in this invention, the resulting cured product was found to excel in both transparency and color.

According to Comparative Example 1 wherein curing took place with benzoyl peroxide and dimethyl p-toluidine, the resulting cured product showed an yellow color.

According to Comparative Example 2 wherein no morpholine derivative was used, the curing time was longer than was the case with the addition of a morpholine derivative.

According to Comparative Example 3 wherein acryloylmorpholine was used in an amount of 0.01 part by weight, the resulting cured product was colorless and transparent, but any effect on increasing the curing rate was not found at all due to a small amount added.

According to Comparative Example 4 wherein 30 parts by weight of acryloylmorpholine were used, the resulting cured product was transparent but, due to an excessive amount added, showed a reddish brown color with a considerable delay in the curing rate.

According to Comparative Example 5 wherein N-acetoacetylmorpholine was used in an amount of 0.01 part by weight, the resulting cured product was colorless and transparent but, due to a small amount added, any effect on increasing the curing rate was not found at all.

According to Comparative Example 6 wherein 30 parts by weight of N-acetoacetylmorpholine were used, the resulting cured product was transparent but, due to an excessive amount added, showed a reddish brown color with a delay in the curing rate.

As mentioned above, this invention provides a method of curing dental resin characterized by polymerizing a polymerizable compound having at least one ethylenically unsaturated double bond, using 1-cyclohexyl-5-ethylpyrimidinetrione as a polymerization initiator, various organometal and organohalogen compounds as promoters and acryloylmorpholine or N-acetoacetylmorpholine as a polymerization aid. With this method, the monomer can be polymerized in a polymerization time shorter than the time of conventional combination of an organoperoxide with an aromatic tertiary amine, giving a cured product excelling in transparency and unlikely to yellow whatsoever. The resulting cured product is also unlikely to discolor in the oral cavity.

In this connection, note that the polymerizable compound having at least one ethylenically unsaturated double bond cannot be polymerized with pyrimidinetrione derivatives other than 1-cyclohexyl-5-ethylpyrimidinetrione, or if somehow polymerized, it takes much time for curing, only to give a cured product which is clouded and so cannot be used for dental purposes. It is also noted that with morpholine derivatives other than acryloylmorpholine and N-acetoacetylmorpholine used as the polymerization aid in this invention, the polymerizable compound having at least one ethylenically unsaturated double bond cannot be polymerized or kept from polymerization, or if somehow polymerized, it gives a cured product which is colored and so cannot be used for dental purposes.

Thus, the rate of polymerization of the monomer using 1-cyclohexyl-5-ethylpyrimidinetrione as the polymerization initiator and various organometal and organohalogen compounds as the promoters can be much more increased by the additional use of acryloylmorpholine or N-acetoacetylmorpholine.

What is claimed is:

1. A method of curing a dental resin by polymerizing
    (A) a polymerizable compound having at least one ethylenically unsaturated double bond in the presence of:
    (B) a morpholine derivative,
    (C) 1-cyclohexyl-5-ethylpyrimidinetrione,
    (D) an organometal compound or compounds selected from the group consisting of acetylacetone copper, copper 4-cyclo-hexyl butyrate, copper acetate, acetylacetone manganese, manganese naphthenate, manganese octylate, acetylacetone cobalt (III), cobalt naphthenate, acetylacetone lithium, lithium acetate, acetylacetone zinc, acetylacetone nickel, nickel acetate, acetylacetone aluminum, acetylacetone calcium, acetylacetone chromium (III), acetylacetone iron (III), sodium naphthenate and rare earth octoate, and
    (E) an organohalogen compound.

2. A method of curing dental resin as claimed in claim 1, wherein the quantity of the morpholine derivative used lies in the range of 0.1 to 15 parts by weight per 100 parts by weight of the polymerizable compound having at least one ethylenically unsaturated double bond.

3. A method of curing dental resin as claimed in claim 1 or 2, wherein the quantity of 1-cyclohexyl-5-ethylpyrimidinetrione used lies in the range of 0.1 to 10 parts by weight per 100 parts by weight of the polymerizable compound having at least one ethylenically unsaturated double bond.

4. A method of curing dental resin as claimed in any one of claims 1-3, wherein the quantity of the organometal compound or compounds used lies in the range of 0.001 to 0.2 parts by weight per 100 parts by weight of the polymerizable compound having at least one ethylenically unsaturated double bond.

5. A method of curing dental resin as claimed in any one of claims 1-4, wherein the quantity of the organohalogen compound used lies in the range of 0.1 to 5 parts by weight per 100 parts by weight of the polymerizable compound having at least one ethylenically unsaturated double bond.

6. A method of curing dental resin as claimed in any one of claims 1-5, wherein the polymerizable compound having at least one ethylenically unsaturated double bond is a monofunctional methacrylate.

7. A method of curing dental resin as claimed in any one of claims 1-5, wherein the polymerizable compound having at least one ethylenically unsaturated double bond is a monofunctional acrylate.

8. A method of curing dental resin as claimed in any one of claims 1-5, wherein the polymerizable compound having at least one ethylenically unsaturated double bond is a polyfunctional methacrylate.

9. A method of curing dental resin as claimed in any one of claims 1-5, wherein the polymerizable compound having at least one ethylenically unsaturated double bond is a polyfunctional acrylate.

10. A method of curing dental resin as claimed in any one of claims 1-9, wherein a filler or fillers is or are additionally used.

* * * * *